(12) United States Patent
Lee et al.

(10) Patent No.: US 7,590,220 B1
(45) Date of Patent: Sep. 15, 2009

(54) X-RAY INSPECTION AND DETECTION SYSTEM AND METHOD

(75) Inventors: Susanne Madeline Lee, Cohoes, NY (US); Peter Michael Edic, Albany, NY (US)

(73) Assignee: General Electric Company, Niskayuna, NY (US)

( * ) Notice: Subject to any disclaimer, the term of this patent is extended or adjusted under 35 U.S.C. 154(b) by 8 days.

(21) Appl. No.: 12/045,110

(22) Filed: Mar. 10, 2008

(51) Int. Cl.
*G01N 23/207* (2006.01)

(52) U.S. Cl. .............................. 378/71; 378/57; 378/75

(58) Field of Classification Search .................. 378/57, 378/70–76
See application file for complete search history.

(56) References Cited

U.S. PATENT DOCUMENTS 7,253,727 B2   8/2007   Jenkins et al.

| | | |
|---|---|---|
| 2006/0071174 A1 | 4/2006 | Spartiotis et al. |
| 2006/0140340 A1 | 6/2006 | Kravis |
| 2007/0263770 A1 | 11/2007 | Harding |
| 2007/0263771 A1 | 11/2007 | Harding |
| 2007/0263772 A1 | 11/2007 | Harding |

*Primary Examiner*—Edward J Glick
*Assistant Examiner*—Mona M Sanei
(74) *Attorney, Agent, or Firm*—Joseph J. Christian

(57) ABSTRACT

An X-ray detection and inspection system is disclosed. The system includes an X-ray source configured to generate an interrogating X-ray beam, wherein the X-ray beam is directed towards a probe volume in a sample, one or more two-dimensional area detectors, wherein the one or more detectors are positioned at angles other than 90 degrees with respect to the direction of the interrogating beam and are configured to receive and detect non-circular conic sections of diffracted X rays from the probe volume, and an acquisition and analysis system configured to generate position and intensity data of the non-circular conic sections such that the corresponding mathematical equations of the conic sections could be generated, to identify one of a quasi-monochromatic or monochromatic XRD pattern from the non-circular conic sections, and to determine a position of the probe volume and at least two Bragg diffraction angles from said XRD pattern.

33 Claims, 9 Drawing Sheets

X-RAY INSPECTION AND DETECTION SYSTEM AND METHOD

BACKGROUND

The invention relates generally to an X-ray inspection system and method, and more particularly to an X-ray inspection system and method for screening.

Many applications use X-ray diffraction to identify the crystal structure and composition of unknown objects spatially distributed along an incident X-ray beam. For example, some airport baggage screening systems use X-ray diffraction (XRD) to identify explosive threats in scanned baggage. When such analyses need to be performed quickly, the standard approach has been to employ energy dispersive X-ray diffraction (EDXRD) with expensive, energy-sensitive, liquid nitrogen (usually) cooled, single pixel, line, or array of line detectors. Frequently these systems employ X-ray sources that generate a divergent, polychromatic, X-ray beam that needs to be collimated and combined with a detector collimator in order to probe a localized volume of space. The size of the localized volume depends on the degree of collimation provided by the collimators. The major problem, therefore, becomes one of measurement time versus spatial resolution. If two collimators are used to provide a reasonable degree of collimation, i.e., good spatial resolution, the photon flux drops dramatically, requiring long measurement times to obtain good counting statistics.

In the case of EDXRD-based explosive detection systems (EDS), for example, both good spatial resolution and fast measurement times are needed. When both source and detector collimators are used, the X-ray intensity is typically reduced by more than 99.99%, leading to low-intensity signals that increase the difficulty of correct explosive threat identification. To compensate for these low signals and address the high false positives and commensurate slow scan rate, EDS manufacturers use single-photon counting, energy-sensitive, single pixel, line, or array of line detectors, e.g., liquid nitrogen cooled, high purity Ge (HPGe, high performance Ge) detectors with small X-ray sensitive areas. An inherent problem with these single-photon counting detectors is their inability to distinguish between two photons of equal energy incident upon the detector simultaneously and a single photon with twice the energy. Mischaracterization of the energy of the incident photon will lead to reduced sensitivity and specificity. Additionally, the detector dark currents (electrical signals recorded with no photons impinging on the detector), which are different for each detector element, are temperature-dependent. At liquid nitrogen temperatures, the dark currents are negligible, but increase non-linearly with increasing temperature. Thus, as the liquid nitrogen boils off and the detector element temperature changes, the dark current increase will not be uniform, degrading the signal across the detector elements differently, which may affect the accuracy of threat detection. The dark current also changes with time as the detectors are exposed to high-energy X rays, possibly affecting the accuracy of threat detection also. Furthermore, the HPGe detectors typically have count rate limitations; they saturate quickly when the diffracting volume contains strongly diffracting crystals, which in turn increases the difficulty of accurate composition identification. Moreover, the operationally acceptable baggage scan rates are such that the counting statistics in the diffracted signal are very low, leading to classification errors.

One solution is to develop more powerful X-ray sources that provide a higher photon flux density. However, most current X-ray sources are already operating near the limit where the target melts, which shortens their lifetime, making source maintenance a concern in explosives detection systems.

Thus, it would be desirable to have an X-ray inspection and detection system having higher accuracy, higher speed, and lower maintenance costs.

BRIEF DESCRIPTION

One embodiment disclosed herein is an X-ray detection and inspection system. The system includes an X-ray source configured to generate an interrogating X-ray beam, wherein the X-ray beam is directed towards a probe volume in a sample, one or more two-dimensional area detectors, wherein the one or more detectors are positioned at angles other than 90 degrees with respect to the direction of the interrogating beam and are configured to receive and detect non-circular conic sections of diffracted X rays from the probe volume, and an acquisition and analysis system configured to generate position and intensity data of the non-circular conic sections such that the corresponding mathematical equations of the conic sections could be generated, to identify one of a quasi-monochromatic or monochromatic XRD pattern from the non-circular conic sections, and to determine a position of the probe volume and at least two Bragg diffraction angles from said XRD pattern.

Another embodiment disclosed herein is a method of X-ray inspection and detection. The method includes generating an interrogating X-ray beam, wherein the X-ray beam is directed towards a probe volume in a sample, interrogating with the X-ray beam at least one voxel within the probe volume to generate diffracted X-rays, detecting non-circular conic sections of diffracted X rays with one or more two dimensional area detectors positioned at an angle other than 90 degrees with respect to the direction of the interrogating X-ray beam, generating the position and intensity data of the non-circular conic sections such that the corresponding mathematical equations of the conic sections could be generated, identifying at least one of a quasi-monochromatic or monochromatic diffraction pattern from the non-circular conic sections, determining the position of the at least one probed voxel by determining at least one apex of at least one diffraction cone corresponding to at least one of the non-circular conic sections of diffracted X rays, and determining at least two Bragg diffraction angles from the at least one of the quasi-monochromatic or monochromatic diffraction pattern.

These and other advantages and features will be more readily understood from the following detailed description of preferred embodiments of the invention that is provided in connection with the accompanying drawings.

DRAWINGS

DETAILED DESCRIPTION

Embodiments of this invention disclose systems and methods for angular dispersive, quasi-monochromatic or monochromatic X-ray interrogation-detection.

In the following specification and the claims that follow, the singular forms "a", "an", and "the" include plural referents unless the context clearly dictates otherwise.

As used herein, the term "quasi-monochromatic or monochromatic X-ray interrogation-detection technique" refers to the combined configuration of an X-ray beam (monochromatic, quasi-monochromatic, or polychromatic) and a two-dimensional (2D) X-ray area detector (narrow or broad energy range) such that monochromatic or quasi-monochromatic XRD patterns are the strongest patterns detected. For example, the use of a monochromatic or quasi-monochromatic X-ray beam with a narrow or broad wavelength range detector, or the use of a polychromatic X-ray source with a narrow wavelength range detector will result in the strongest detected XRD patterns being quasi-monochromatic or monochromatic ones. Alternatively, the combination of two different restricted energy X-ray beams, a 2D area detector with either a narrow or broad energy sensitivity, and post-processing of the detected XRD patterns can result in the generation of a quasi-monochromatic XRD pattern. For example, two different K-edge filters could be used to create the two different restricted energy X-ray beams. In more detail, to create a quasi-monochromatic XRD spectrum with 60 keV±0.5 keV X rays, one pattern could be created with an Er K-edge filter in the interrogating X-ray beam, while the other pattern could be created with a Yb filter in the interrogating X-ray beam. With appropriate filter thicknesses, when the two XRD patterns are subtracted one from the other (Yb—Er), all but the X-ray energies between the two K-edge filters will be suppressed leaving a quasi-monochromatic XRD pattern created with predominantly 60 keV X rays. This technique has the distinct advantage of transmitting up to about 70% of the 60 keV source photons, a significant improvement over conventional monochromator crystals.

Figure 1:
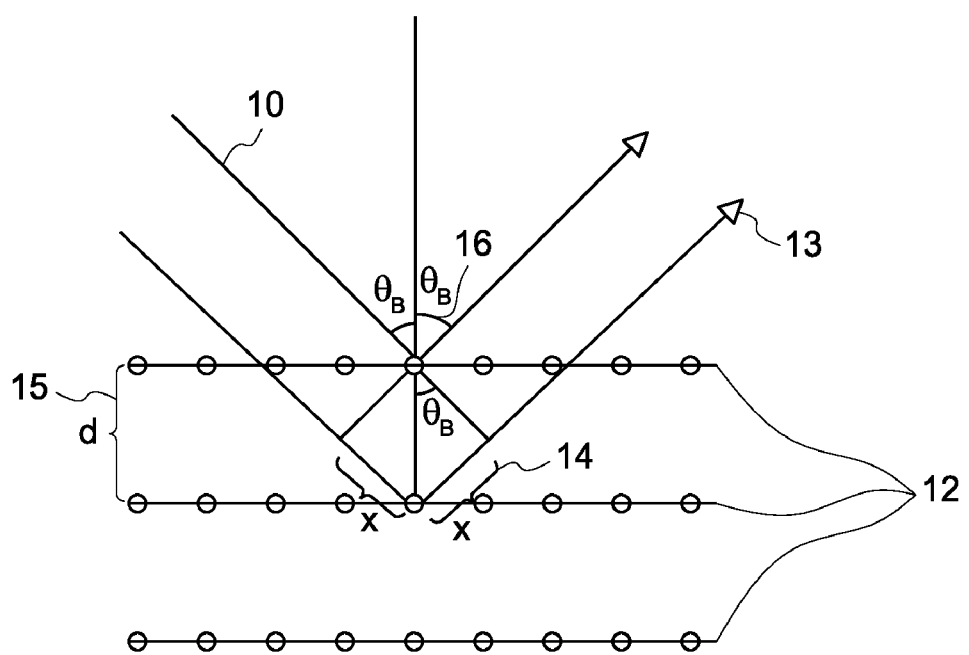
FIG. 1 is a schematic representation of X-ray diffraction from planes of atoms or molecules in a crystal.

FIG. 1 is a schematic representation of X-ray diffraction from crystal planes. X-ray diffraction from crystal planes is well known in the art and the diffraction characteristics are governed by Bragg's law, given in equation (1) for first order diffraction.

$$\lambda = 2d \sin \theta_B \tag{1}$$

where $\lambda$ is the wavelength of the incident X rays, $\theta_B$ is the Bragg angle at which the diffracted intensity is a maximum, and "d" is the spacing between planes of atoms or molecules in the material. Rewriting equation (1), d is given by $$d = \lambda/(2 \sin \theta_B) \tag{2}$$

$$d = hc/(2E \sin \theta_B) \tag{3}$$

where E is the energy of the X rays, c is the velocity of light in vacuum, and h is Planck's constant. Therefore, measuring $\theta_B$ and knowing the energy of the interrogating X rays will enable determination of the spacing between planes of atoms or molecules in a material and the material's crystal structure, uniquely identifying the material.

When X rays 10 are incident on planes of atoms or molecules 12 in the material, the X rays are diffracted by the various planes as shown in FIG. 1. The diffracted X rays 13 interfere coherently if the path difference 14 ("x"+"x"=2 d sin $\theta_B$) between adjacent planes is an integral multiple of the wavelength of the interrogating X-rays. The spacing "d" 15 between the planes of atoms or molecules 12 can be determined by measuring the diffraction angle 16 ($\theta_B$) if the energy of the interrogating X rays is accurately known.

Figure 2:
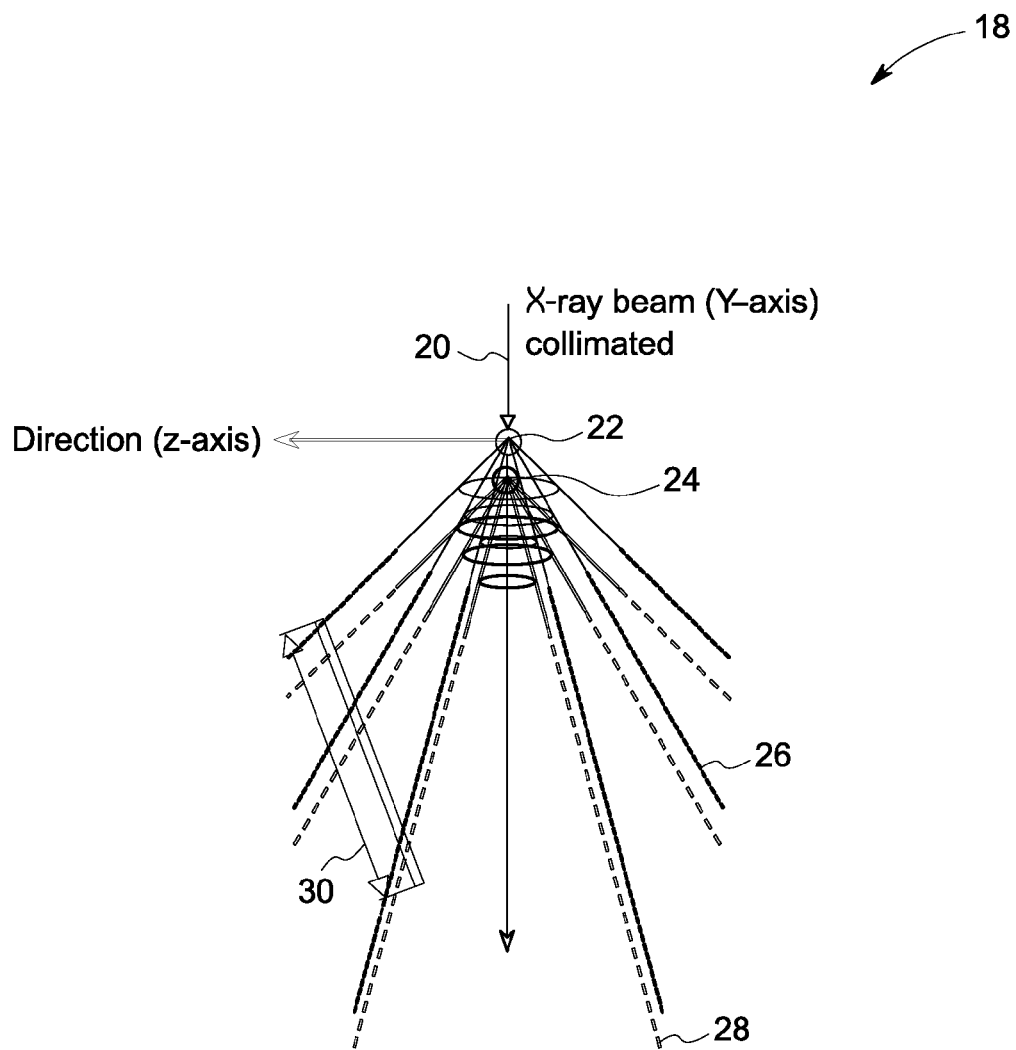
FIG. 2 is a schematic representation of an angular dispersive quasi-monochromatic or monochromatic X-ray interrogation-detection system in accordance with an embodiment of the invention.

FIG. 2 is a schematic representation of an angular dispersive, quasi-monochromatic or monochromatic, X-ray interrogation-detection system 18 in accordance with an embodiment of the invention. In the illustrated embodiment, a collimated X-ray beam 20 is incident on sample volumes 22 and 24 generating diffraction cones, of which 26 (cone of solid lines pointed to by element number 26) and 28 (cone of dashed lines pointed to by element number 28) are representative, respectively. A detector 30 is placed along a plane such that diffracted conic sections other than circles are captured on the detector 30. A conic section is formed from the intersection of a plane and a cone.

The diffraction pattern in this scenario consists of parabolas, hyperbolas, and/or ellipses resulting from the intersection of the diffracted X-ray cones with the obliquely angled plane of the detector. The diffraction cones can be characterized by the equation $$x^2 + z^2 - a^2(y - y_0)^2 = 0, \tag{5}$$

where $y_0$ is the position of the diffracting volume, $a = \tan 2\theta_B$, and $\theta_B$ is the Bragg diffraction angle.

Intersecting the diffraction cones with a plane made by, for example, a flat panel digital X-ray detector or a flat piece of X-ray film will result in various conic sections being recorded by the detector or on the film, depending on the angle between the detection plane and the cone axis. If the detection plane is perpendicular to the axis of the diffracted cones, the resulting conic sections will be circles. It is possible to have two spatially separated sample volumes of different composition that will produce coincident x-ray diffraction circles. In other words, the diffracted circles are not unique to the diffracting volume in this scenario. This can be seen from the following equations. Let the equation that represents the plane of the detector perpendicular to the interrogating X-ray beam be:

$$y = H, \tag{6}$$

where H is the distance between the X-ray source focal point and the detector plane. This distance can be measured accurately. Substituting Equation (6) into Equation (5) results in the equation of the diffraction circles on the detection plane:

$$x^2 + z^2 = a^2(H - y_0) \tag{7}$$

The quantity $a(H - y_0)$ is the radius of the diffraction circles. To see that it is possible to have two spatially separated diffracting volumes produce diffraction circles of the same radius, consider the case of a diffracting volume closer to the source (smaller $y_0$) than a second diffracting volume. The first diffracting volume's larger sample to detector distance will result in a larger ($H - y_0$) than for the second diffracting volume. If the atomic planes in the first diffracting volume are selected appropriately, $a=\tan 2\theta_B$ may be smaller by just enough to compensate precisely for the larger $(H-y_0)$, resulting in a diffraction circle radius that is exactly the same as a diffraction circle radius for the second diffracting volume. Thus, diffraction circles cannot be used to uniquely identify the voxel from which the X rays diffracted.

When the detection plane is not perpendicular to the axis of the diffracted cones, the resulting conic sections are unique; no other sample volume or composition can produce the same (non-circular) conic section. For example, let the detection plane be parallel to the X-axis and oriented such that the equation of the detection plane is given by:

$$y=H-|m|z, \qquad (8)$$

where the slope of the plane with respect to the Z-axis is $-|m|$ and H is the intersection of the plane with the Y-axis. This plane intercepts cones given by Equation (5) in non-circular conic sections with equations:

$$x^2+(1+a^2m^2)z^2+2a^2(H-y_0)|m|-a^2(H-y_0)^2=0 \qquad (9)$$

Figure 3:
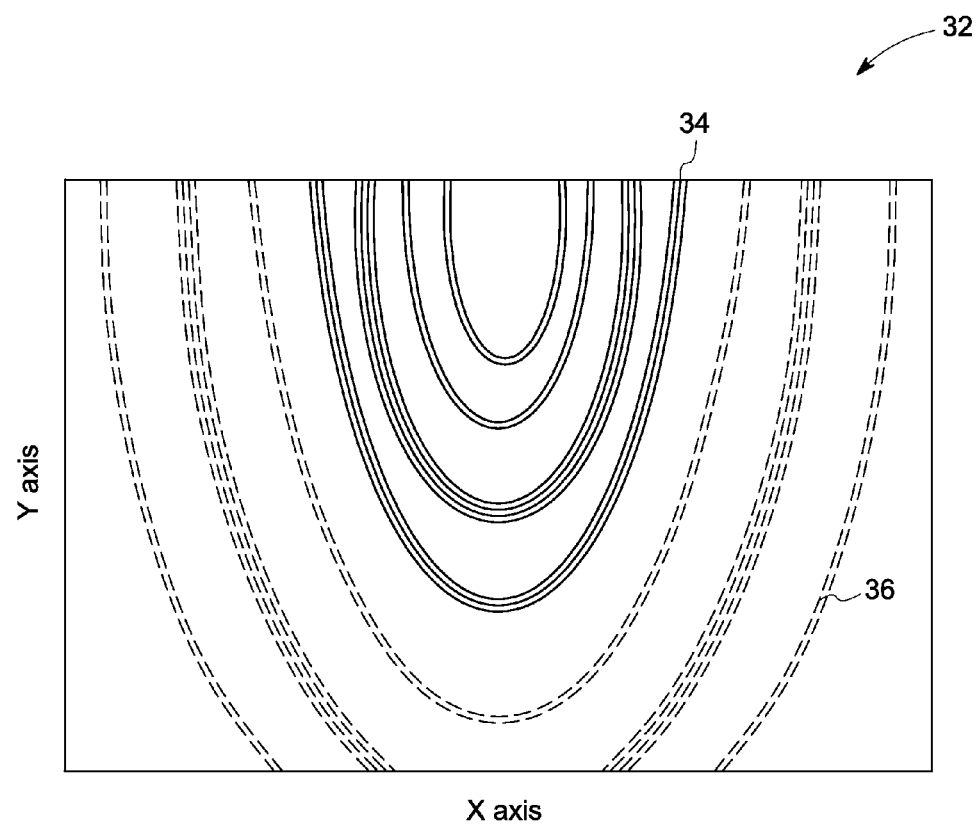
FIG. 3 is a schematic representation of conic sections formed in an angular dispersive quasi-monochromatic or monochromatic X-ray interrogation-detection technique in accordance with an embodiment of the invention.

According to equation (9), it is not possible for "a" which is related to the Bragg angle and hence the composition of the material and "$y_0$", which is the position of the diffracting volume, to compensate for each other exactly, keeping the shape of the conic section the same, because the $z^2$ and z terms do not contain combinations of a and $(H-y_0)$ only, as in the equation of the circle. Thus, extracting the appropriate parameters from the non-circular conic sections uniquely identifies both the position ($y_0$) of the small sample volume off which the X rays diffracted and the composition (related to $\theta_B$) of that small sample volume. FIG. 3 schematically illustrates conic sections 32 formed using this angular-dispersive, quasi-monochromatic or monochromatic, X-ray interrogation-detection technique in accordance with an embodiment of the invention. The solid lines 34 represent the diffracted conic sections from a first material and the dashed lines 36 represent those from a second material. Depending on the location of the sample volumes and their respective compositions, the conic sections 34 may be interleaved with, but still distinguishable from, conic sections 36. Alternatively, the conic sections 34 may even intersect the conic sections 36.

Working from the equations for the conic sections and the detector plane, the equation of the diffraction cones that gave rise to the detected non-circular conic sections are uniquely determined, i.e. the cone angles and spatial positions of each cone vertex are uniquely determined from each non-circular conic section. The spatial positions of the cone vertices determine the diffracting sub-volume (hereinafter referred to as a volume pixel or a voxel). Cones having a common apex spatially identify the position of the voxel from which the X rays diffracted, producing the detected diffraction pattern. Thus, no detector collimator is required to establish the voxel's spatial position, as is required in conventional energy-dispersive XRD.

Standard intensity versus two-theta plots for comparison to material databases can be generated from the conic sections, by selecting only those conic sections that correspond to cones with a common apex, integrating the photon intensities contained in each of these conic sections, determining relative integrated intensities, and graphing those relative intensities as a function of half the corresponding cone angle, i.e. $2\theta_B$, for that conic section. Comparing such plots to standard XRD material databases enables fast determination of voxel composition. In summary, with the appropriate oblique angling of a flat area detector and simple three-dimensional geometrical considerations, both the spatial position of an object and its composition can be rapidly determined. Objects dispersed along a wide range of distances can be distinguished easily from each other and their crystal structure and composition can be identified from the cone angles and interrogating X-ray energy. Integrating the X-ray intensities over the whole conic section increases the signal to noise ratio for a given Bragg diffraction angle, which increases the sensitivity and specificity of object identification. Additionally, if the signal to noise ratio increases sufficiently, the baggage scan rate can be increased without loss in sensitivity and specificity.

Some embodiments of the invention described here address issues of confounding diffraction patterns in conventional monochromatic X-ray diffraction (XRD) when unknown objects are distributed randomly in space along small (hundreds of micrometers) or large distances (more than 1 centimeter) of the X-ray beam. Embodiments of the invention alter the conventional monochromatic XRD detector placement (perpendicular to the undiffracted X-ray beam for an area detector) to positions that make angles other than 90° with the undiffracted X-ray beam. In one embodiment, the angle is chosen such that the smallest and largest potential diffraction cones intersect the detector, ensuring that all important lattice planes are imaged. With this angled detector, the diffraction patterns are non-circular conic sections: hyperbolas, parabolas, and ellipses.

Figure 4:
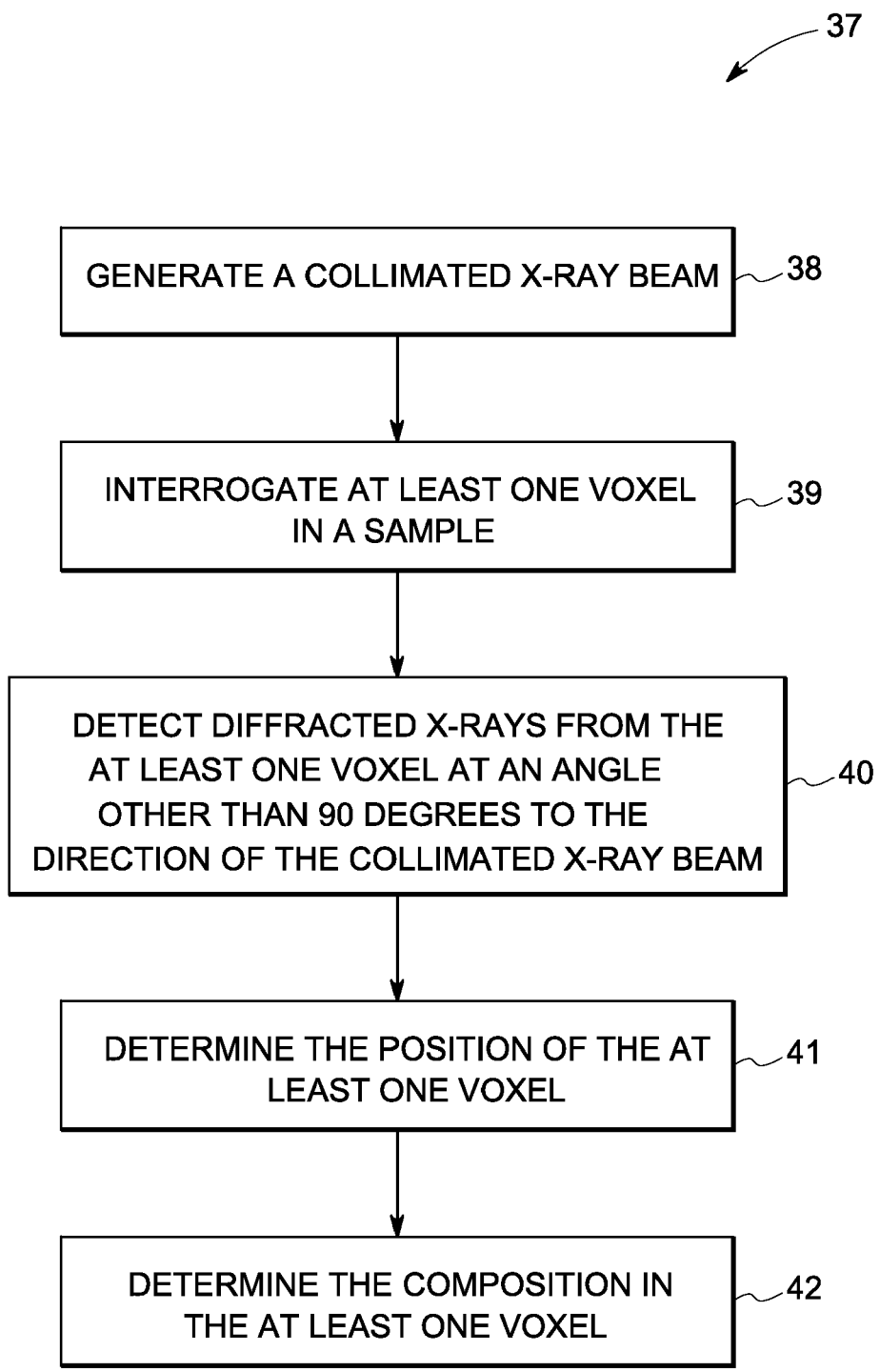
FIG. 4 is a flow chart representation of an angular dispersive quasi-monochromatic or monochromatic X-ray interrogation-detection method in accordance with an embodiment of the invention.

FIG. 4 is a flow chart representation of an angular-dispersive, quasi-monochromatic or monochromatic, X-ray interrogation-detection method 37 in accordance with an embodiment of the invention. The method includes generating a collimated beam of X-rays 38.

In one example, a collimated beam may be formed by using a physical collimator, which, for example, may create the collimated beam by blocking divergent X rays from reaching the object under interrogation. Alternatively, an X-ray optic may be used to collimate the beam, wherein divergent X rays may be redirected to form a collimated beam.

The collimated X-ray beam is used to interrogate at least one voxel in a sample in step 39. The interrogation of the at least one voxel results in the generation of at least one cone of X-rays. In step 40, the at least one cone of diffracted X-rays from the at least one voxel is detected by a 2D area detector placed at an oblique angle to the incident X-ray beam direction. Many signal processing techniques can be used to analyze the detector signals and determine the equations of the non-circular conic sections therein. For example, a collection of proposed conic sections or paths may be generated and the measured detector signals correlated along the length of the proposed sections. By varying the parameters of the proposed non-circular conic sections and considering maxima in the correlated signals, a best-fit equation to the non-circular conic sections can be made. From the detected and recorded conic sections, the apices of the conic sections are determined in step 41. The coincident conic section apices are used to locate the spatial position of the probed sample volume. In step 42, from the detected conic sections, the Bragg diffraction angles are also determined. Once at least two Bragg diffraction angles are determined, the characteristic spacings between planes of atoms or molecules in the voxel can also be determined as discussed above, thus identifying the composition of the material in the at least one probed voxel.

In one embodiment, the detector is configured to receive and detect non-circular conic sections of diffracted X-rays originating from the probe volume. Position and intensity data of the detected conic sections are generated from the detector signals. The combination of interrogating X-ray energies and/or energy sensitivity of the detector may be used to transform the detected X-ray diffraction pattern into a quasi-monochromatic or monochromatic diffraction pattern. The position and intensity data of the conic sections are characterized and analyzed to determine the position of the probed volume and at least two Bragg diffraction angles.

Figure 5:
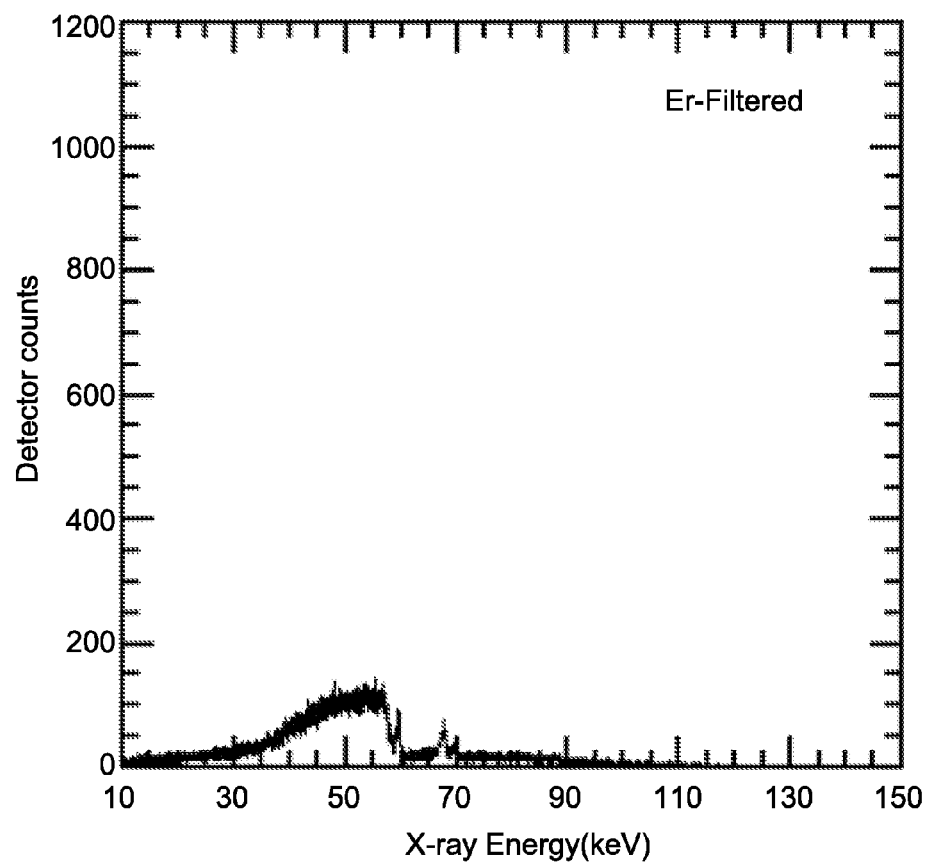
FIG. 5 is an energy spectrum of an X-ray beam that has been filtered with an Er K-edge filter in accordance with an embodiment of the invention.
Figure 6:
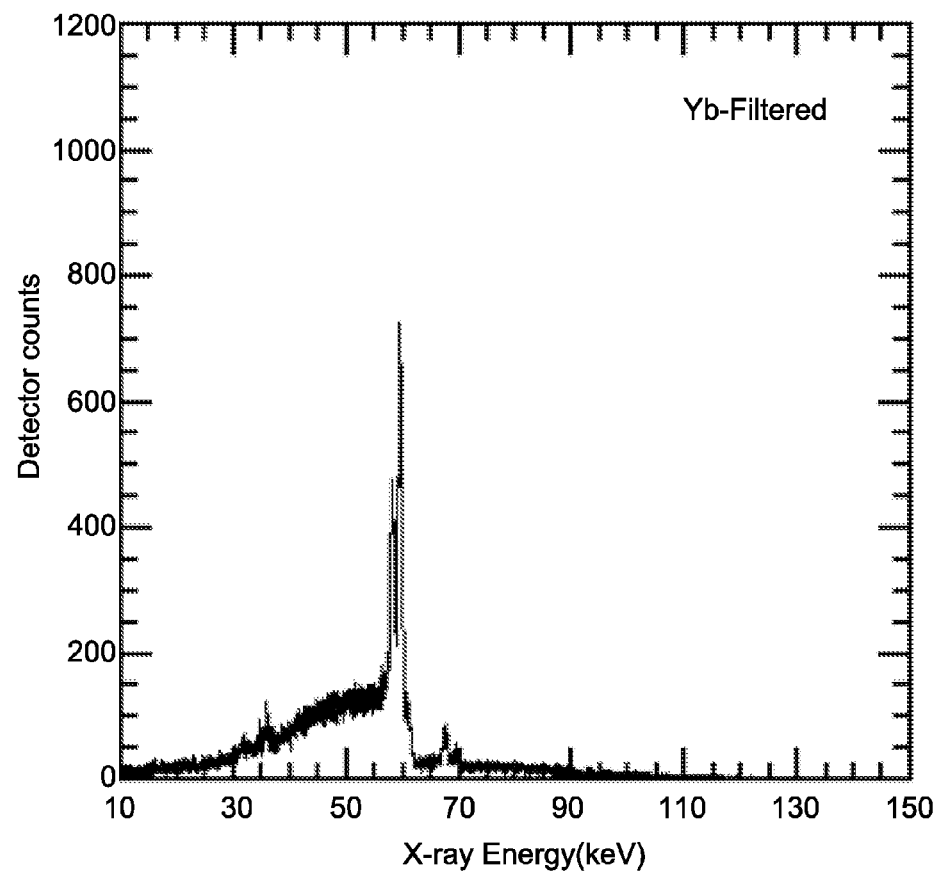
FIG. 6 is an energy spectrum of an X-ray beam that has been filtered with a Yb K-edge filter in accordance with an embodiment of the invention.
Figure 7:
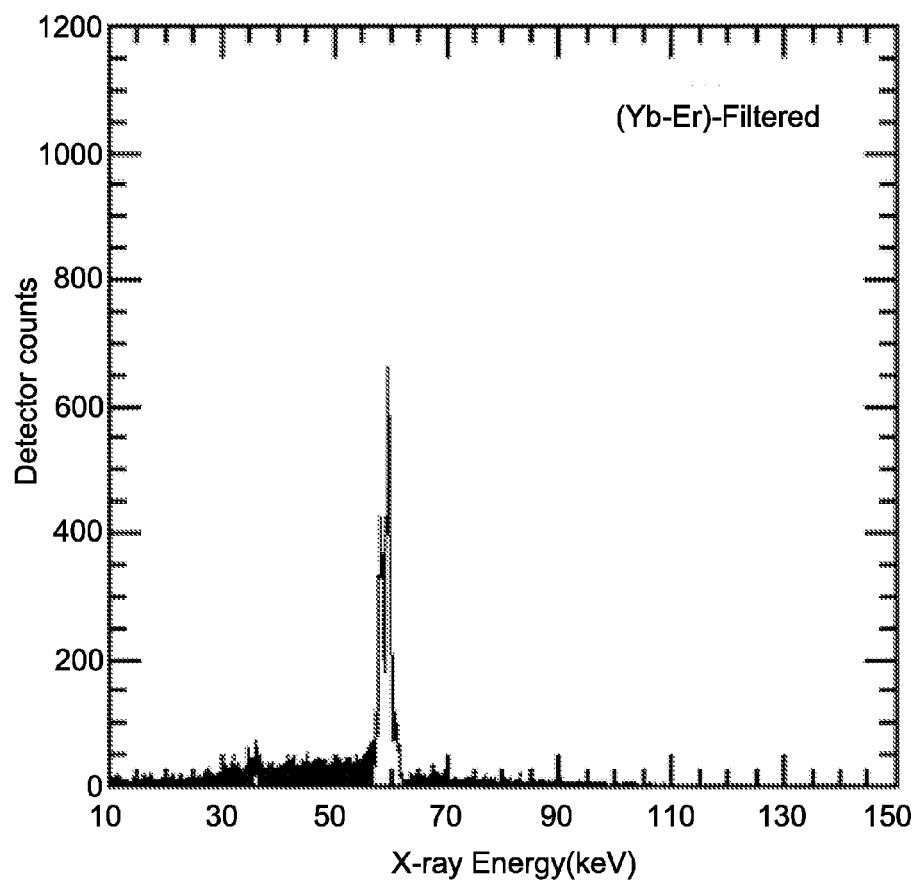
FIG. 7 is the difference between the Yb- and Er-filtered spectra in accordance with an embodiment of the invention.
Figure 8:
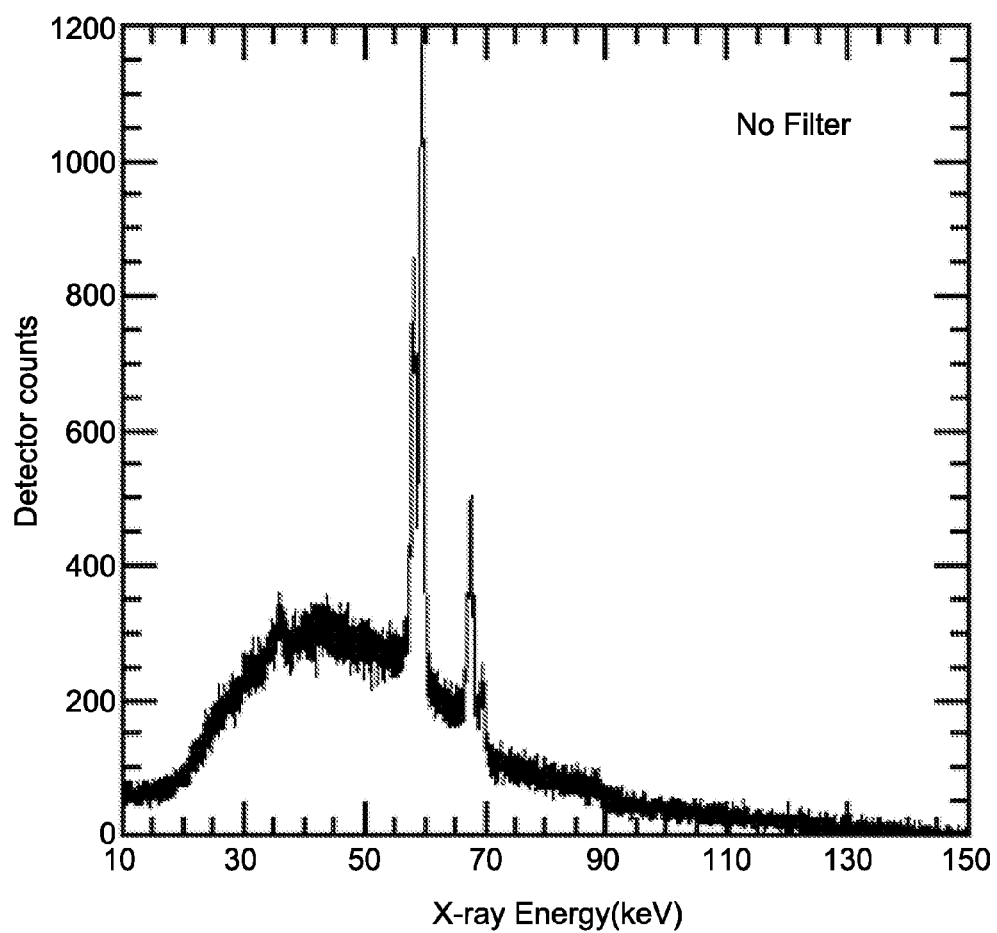
FIG. 8 is an energy spectrum of an unfiltered X-ray beam in accordance with an embodiment of the invention.

In one example, the energy distribution of the interrogating X-ray beam used in some embodiments of the invention may be about a few eV wide (called monochromatic). In one alternate example, the energy distribution in the interrogating X-ray beam may be about one to about a few keV wide (called quasi-monochromatic). In one embodiment, the interrogating X-ray beam may be polychromatic and may have emissions in an energy range from about a few keV to about 200 keV or higher. In one example, a combination of filters may be used to select a characteristic wavelength, such as $W-K_\alpha$, from a polychromatic spectrum generated from a tungsten (W) target. Conventionally, this type of a narrow energy distribution X-ray beam is achieved by diffracting the polychromatic X-ray output of a laboratory source off a strained monochromator crystal. Such a monochromator usually reduces significantly the interrogating beam intensity, typically between one and several orders of magnitude less than the original source intensity. With the filter technique, the polychromatic output of a laboratory X-ray source is passed through a K-edge filter e.g., Er with an absorption edge just below the desired characteristic X-ray energy, e.g., 60 keV. This transmits X-ray energies below and above the absorption edge, as shown in FIG. 5. Next this process is repeated with a different K-edge filter, e.g., a Yb filter having an absorption edge at a slightly higher energy than the desired energy (60 keV, in our example), shown in FIG. 6. If the filter thicknesses are chosen correctly, all but the X-ray energies between the two K-edge filters will be suppressed. Thus, when the two diffraction patterns recorded with the two different K-edge filters are subtracted from each other (Yb filtered pattern–Er filtered pattern), the resulting XRD pattern will be due to X-rays within the narrow range between the K-edges of the two filters, as shown in FIG. 7. The advantage of this technique is that the intensity of the X rays in this narrow range may be up to about 70% that of the unfiltered source spectrum, shown in FIG. 8, and at least an order of magnitude more intense than that produced with conventional monochromator crystals.

In another example, the spectral shaping ability of total internal reflection (TIR) X-ray optics, such as polycapillary optics or multilayer thin film TIR optics described in co-pending U.S. patent application Ser. No. 11/619,009, can be used to generate a collimated, quasi-monochromatic beam from a polychromatic beam.

In another example, diffractive optics, such as curved multilayer thin film diffractive optics or doubly curved crystal optics or any number of other diffracting crystal optics, may be used to generate a collimated, monochromatic or quasi-monochromatic, interrogating, X-ray beam from a polychromatic X-ray source.

Embodiments of the invention include systems with 2D area detectors. Detector sensitivity to incident X-ray wavelengths may be broad, such as standard energy-integrating 2D area detectors (e.g. flat panel, multiwire, CCD, film), or narrow, such as energy-sensitive CdTe or CZT-type 2D, multiple pixel, area detectors described, for example, in US Patent publication US20060071174. For example, an X-ray detector may have sensitivity to a broad range of energies, from about a few keV to 200 keV or higher, in which case the interrogating X-ray beam should contain limited X-ray energies or the filter subtraction method described earlier should be employed in order to produce a quasi-monochromatic or monochromatic XRD pattern. In one alternate example, the detector may be sensitive to a narrower energy range, such as 60 keV plus or minus 2 keV, in which case a broad polychromatic X-ray beam could be used to interrogate the sample and create a quasi-monochromatic XRD pattern.

Although the following example application of an angular dispersive quasi-monochromatic or monochromatic X-ray interrogation-detection technique is described in detail in the context of a baggage screening system, embodiments of the invention are not limited to baggage screening systems. Other systems using this technique to inspect or detect all animate or inanimate objects fall within the scope of this invention. For example, the system can also used be to screen, for example, passengers, to probe for any hidden explosive or contraband being transported. In another example, cargo containers can be screened using this technique. In one embodiment, the system could be mounted on one or more robotic arms to move the system to the position of an object to be inspected. In a non-limiting embodiment, suitable X-ray energies for inspecting cargo containers may be in the MeV range.

Further, the detection and inspection systems described herein have several applications including inspection or defect analysis of rail or aircraft or automotive parts. In one example, such parts may be composite parts. In a non-limiting embodiment, suitable X-ray energies for such analysis may be in the hundreds of keV range. The system can also be used to inspect parts such as but not limited to railroad tracks, where a crystal structure in a material has been altered due to environmental factors such as stress or temperature.

Figure 9:
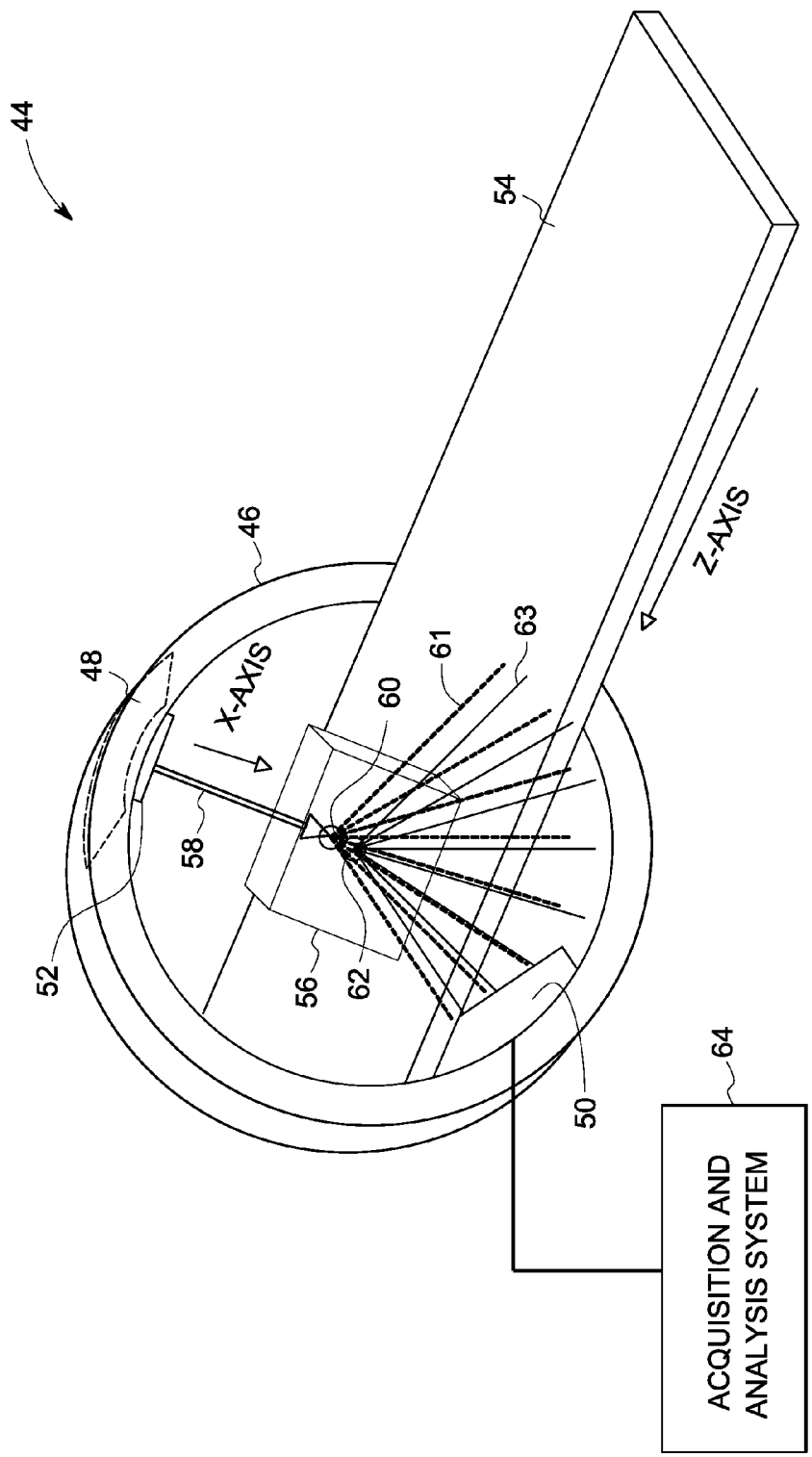
FIG. 9 is a schematic representation of an angular dispersive quasi-monochromatic or monochromatic X-ray interrogation-detection baggage screening system in accordance with an embodiment of the invention.

FIG. 9 is an illustrated embodiment of an angular dispersive quasi-monochromatic or monochromatic X-ray interrogation-detection baggage screening system 44. The screening system 44 includes an X-ray source 48 and detector 50 integrated or mounted onto a frame or gantry 46. In the illustrated embodiment, a collimator 52 is used to collimate the X-ray beam output of the source 48. In a non-limiting example, the beam width may be about 2 mm. Non-limiting examples of X-rays sources include Brehmsstrahlung radiation sources.

The source and detector are positioned such that diffracted X-rays from an interrogated volume are detected at an angle other than 90 degrees from the collimated X-ray beam 58. In a non-limiting example, one or more flat-panel digital X-ray detectors may be used. In one example, the gantry 46 may be circular as illustrated in FIG. 9. In some embodiments, the circular frame may be rotary, allowing for the rotation of the X-ray source and one or more detectors in combination or independently of each other. In another non-limiting example, the frame may be rectangular with multiple sources and one or more detectors distributed around the stationary frame.

A conveyer system 54 moves a sample 56 to be probed such as a piece of baggage into an interrogation region located within the gantry 46. The collimated X-ray beam 58 interrogates baggage voxels 60 and 62, which generate representative diffraction cones 61 and 63, respectively, with the cone apices located at the baggage voxels 60 and 62. Detector 50, placed at an angle other than 90 degrees with respect to the direction of the interrogating X-ray beam, detects the non-circular conic sections produced by the intersection of the diffraction cones with the plane of the detector. Thus, the detected conic sections are hyperbolas, parabolas, and ellipses.

Data from the detector 50 is acquired by an acquisition and analysis system 64, which curve fits the detected conic sections and determines the voxel from which the diffracted X rays originated. Once the voxel position is determined and combined with the curve-fitted data, the spacings between the planes of atoms or molecules in the voxel and the voxel's crystal structure can be found, determining the voxel's composition.

The equations of the diffraction cones can be uniquely determined from the non-circular conic sections recorded on the angled detector. The equations of the diffraction cones are used to determine the spatial position of the diffracting volume in the baggage. Diffraction cones with common apices determine which conic sections in the pattern correspond to a single diffracting object and identify the position of the voxel that diffracted the X-rays into those cones. From the equations of the conic sections corresponding to a single diffracting voxel, the Bragg diffraction angles (one quarter the cone angle) are determined, which in turn determine the material crystal structure and atomic or molecular plane spacings. The structure and plane spacings then determine the voxel's composition according to standard crystallography theory. Alternatively, once the Bragg diffraction angles have been determined, the standard intensity versus two-theta plots can be generated and compared to XRD material databases to identify material composition. For example, explosive and contraband material in a piece of baggage can be identified using embodiments of the systems and methods described herein.

In one embodiment, the baggage screening system described herein may be used in combination with a computed tomography (CT) system. The CT system can be used as a primary scanning device to identify regions of interest from a bigger volume. The angular dispersive quasi-monochromatic or monochromatic X-ray interrogation-detection part of the baggage screening system can then be used in accordance with embodiments of the invention to scan the regions of interest identified with CT and determine the material compositions in those regions. In an alternate embodiment, the baggage screening system described herein may be used in combination with an X-ray radiography system, which identifies regions of interest in the bigger volume.

Embodiments of the invention are expected to enable reduced system and maintenance costs. On the system side, energy-integrating 2D area detectors are typically less expensive than the energy-sensitive, single pixel, line, or array of line detectors currently used in XRD baggage scanning and, by eliminating the detector collimator required by EDXRD-explosive detection systems, the system design is simplified. Eliminating the need for cryogenic detector cooling allows for simpler and more flexible system designs, while reducing system size, as well as system and maintenance costs. Additionally, the X-ray detection area of an energy-integrating 2D area detector can be so much larger than that of the energy-sensitive detector that, after integrating the intensity along a path representing each conic section, significantly better signal to noise in the detected signal can be achieved in less time than with the energy-sensitive detection technique. In baggage scanning applications, for example, the improved signal to noise in detected signals would enable higher baggage scanning rates with improved sensitivity and specificity.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims. For example, although the method has been described in the context of two diffracting volumes being probed by the collimated X-ray beam, the system and method are applicable to one or more diffracting volumes interrogated by the collimated X-ray beam.

What is claimed as new and desired to be protected by Letters Patent of the United States is:

1. An X-ray detection and inspection system comprising:
    an X-ray source configured to generate an interrogating X-ray beam, wherein the X-ray beam is directed towards a probe volume in a sample;
    one or more two-dimensional (2D) area detectors, wherein the one or more detectors are positioned at angles other than 90 degrees with respect to the direction of the interrogating beam and are configured to receive and detect non-circular conic sections of diffracted X-rays from the probe volume; and
    an acquisition and analysis system configured to generate position and intensity data of the non-circular conic sections such that corresponding mathematical equations of the non-circular conic sections are generated, to identify one of a quasi-monochromatic or monochromatic XRD pattern from the non-circular conic sections, and to determine a position of the probe volume and at least two Bragg diffraction angles from said XRD pattern.

2. The system of claim 1, wherein the one or more detectors comprise one or more detectors selected from the group consisting of energy-integrating 2D area detectors, energy-discriminating 2D area detectors, and combinations thereof.

3. The system of claim 1, wherein the acquisition and analysis system is configured to determine at least two characteristic spacings between planes of atoms or molecules in the probe volume from the at least two Bragg diffraction angles.

4. The system of claim 3, wherein the acquisition and analysis system is configured to determine a material composition from the at least two characteristic planar spacings.

5. The system of claim 1, wherein a collimator is used to collimate the interrogating X-ray beam.

6. The system of claim 5, wherein the collimator is an x-ray optic.

7. The system of claim 1, wherein the X-ray beam is configured to be one of a monochromatic, quasi-monochromatic, or polychromatic X-ray beam.

8. The system of claim 1, further comprising at least two different K-edge filters used sequentially, wherein the X-ray beam is a polychromatic beam and wherein the acquisition and analysis system is configured to generate the quasi-monochromatic X-ray diffraction pattern by subtracting diffraction patterns generated by each of the at least two K-edge filters individually.

9. The system of claim 1, wherein the 2D area detector has a narrow wavelength range sensitivity.

10. The system of claim 1, wherein the 2D area detector has a broad wavelength range sensitivity.

11. The system of claim 1, wherein the energy or energies of the interrogating X-ray beam are selected to be in a range from about 1 keV to about 5 MeV.

12. The system of claim 1, wherein an overlapping energy width of the interrogating X-ray beam and the detector is in a range from about 1 keV to 5 keV.

13. The system of claim 1, wherein an overlapping energy width of the interrogating X-ray beam and the detector is in a range from about 1 eV to 1 keV.

14. The system of claim 1, wherein the system is a screening system.

15. The system of claim 14, wherein the screening system is a baggage or cargo screening system.

16. The system of claim 15, wherein the system is configured to detect and identify explosive or contraband material within the probe volume.

17. The system of claim 14, comprising a frame wherein one or a plurality of sources and detectors are distributed around the frame, and wherein the frame is one of a stationary or rotary frame.

18. The system of claim 1, wherein the system is a defect inspection system for auto, rail, or aircraft parts.

19. The system of claim 1, wherein the system is combined with at least one of a CT or radiographic system, which facilitates identification of regions of interest.

20. A method of X-ray inspection and detection comprising:
generating an interrogating X-ray beam, wherein the X-ray beam is directed towards a probe volume in a sample;
interrogating at least one voxel within the probe volume by the X-ray beam to generate diffracted X-rays;
detecting non-circular conic sections of diffracted X-rays with one or more 2D area detectors positioned at an angle other than 90 degrees with respect to the direction of the interrogating X-ray beam;
generating position and intensity data of the non-circular conic sections such that corresponding mathematical equations of the conic sections are generated;
identifying at least one of a quasi-monochromatic or monochromatic diffraction pattern from the non-circular conic sections;
determining a position of the at least one probed voxel by determining at least one apex of at least one diffraction cone corresponding to at least one of the non-circular conic sections of diffracted X-rays; and
determining at least two Bragg diffraction angles from the at least one of the quasi-monochromatic or monochromatic diffraction pattern.

21. The method of claim 20, wherein the one or more detectors comprise one or more detectors selected from the group consisting of energy-integrating 2D area detectors, energy-discriminating 2D area detectors, and combinations thereof.

22. The method of claim 20, comprising collimating the X-ray beam using a collimator.

23. The method of claim 22, wherein the collimator is an x-ray optic.

24. The method of claim 20, comprising determining at least two characteristic spacings between planes of atoms or molecules in the probe volume from the at least two Bragg diffraction angles.

25. The method of claim 24, comprising determining the material composition from the at least two characteristic planar spacings.

26. The method of claim 20, wherein the interrogating X-ray beam is one of a monochromatic, quasi-monochromatic, or polychromatic X-ray beam.

27. The method of claim 20, wherein generating and characterizing position and intensity data of the quasi-monochromatic diffraction pattern comprises subtracting diffraction patterns generated using at least two different K-edge filters, wherein the interrogating X-ray beam is a polychromatic beam.

28. The method of claim 20, wherein the 2D area detector has a narrow wavelength range sensitivity.

29. The method of claim 20, wherein the 2D area detector has a broad wavelength range sensitivity.

30. The method of claim 20, wherein the energy or energies of the interrogating X-ray beam are selected to be in a range from about 1 keV to about 5 MeV.

31. The method of claim 20, wherein an overlapping energy width of the interrogating X-ray beam and the detector is in a range from about 1 keV to 5 keV.

32. The method of claim 20, wherein an overlapping energy width of the interrogating X-ray beam and the detector is in a range from about 1 eV to 1 keV.

33. The method of claim 20, wherein method is combined with a method to identify a region of interest from data acquire from at least one of a CT or radiographic system.

* * * * *